(12) United States Patent
Flick

(10) Patent No.: US 6,606,754 B1
(45) Date of Patent: Aug. 19, 2003

(54) SUPPORTED HYPO/HYPERTHERMIA PAD

(75) Inventor: Roland E. Flick, Elma, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 0 days.

(21) Appl. No.: 09/542,010

(22) Filed: Apr. 3, 2000

Related U.S. Application Data

(60) Provisional application No. 60/128,433, filed on Mar. 30, 1999.

(51) Int. Cl.$^7$ ................................................ A47C 21/04
(52) U.S. Cl. .................. 5/421; 5/423; 5/652.2; 5/654
(58) Field of Search .................. 5/652.1, 652.2, 5/654, 655.5, 421, 423, 714, 909

(56) References Cited

U.S. PATENT DOCUMENTS

| | | | | |
|---|---|---|---|---|
| 2,913,833 A | * | 11/1959 | Glintz | 34/97 |
| 3,083,381 A | | 4/1963 | Bailey | 5/347 |
| 3,266,064 A | | 8/1966 | Figman | 5/347 |
| 3,444,922 A | * | 5/1969 | Dingman | 5/423 |
| 3,681,797 A | * | 8/1972 | Messner | 5/421 |
| 3,778,851 A | | 12/1973 | Howorth | 5/347 |
| 4,057,861 A | | 11/1977 | Howorth | 5/365 |
| 4,073,021 A | * | 2/1978 | Carlisle | 5/654 |
| 4,132,262 A | | 1/1979 | Wibell | 165/26 |
| 4,825,868 A | * | 5/1989 | Susa et al. | 5/421 |
| 4,884,304 A | | 12/1989 | Elkins | 5/421 |
| 5,002,336 A | * | 3/1991 | Feher | 297/180.13 |
| 5,195,199 A | * | 3/1993 | Sereboff | 5/654 |
| 5,269,369 A | | 12/1993 | Faghri | 607/104 |
| 5,329,096 A | * | 7/1994 | Suematsu | 219/528 |
| 5,456,701 A | | 10/1995 | Stout | 607/104 |
| 5,561,875 A | | 10/1996 | Graebe | 5/423 |
| 5,715,695 A | * | 2/1998 | Lord | 5/423 |
| 5,730,120 A | | 3/1998 | Yonkers, Jr. | 128/202.13 |
| 5,749,111 A | * | 5/1998 | Pearce | 5/652 |
| 5,774,916 A | | 7/1998 | Kurhi | 5/632 |
| 5,785,716 A | | 7/1998 | Bayron et al. | 607/108 |
| 5,787,534 A | | 8/1998 | Hargest et al. | 5/726 |
| 5,794,289 A | * | 8/1998 | Wortman et al. | 5/423 |
| 5,800,480 A | | 9/1998 | Augustine et al. | 607/96 |
| 5,837,002 A | | 11/1998 | Augustine et al. | 607/104 |
| 5,887,304 A | | 3/1999 | von der Heyde | 5/726 |
| 5,926,884 A | * | 7/1999 | Biggie et al. | 5/714 |
| 6,049,927 A | * | 4/2000 | Thomas et al. | 5/421 |
| 6,082,683 A | * | 7/2000 | Yates | 248/118.1 |
| 6,119,474 A | | 9/2000 | Augustine et al. | 62/259.3 |
| 6,171,333 B1 | * | 1/2001 | Nelson et al. | 5/652.1 |

\* cited by examiner

*Primary Examiner*—Lynne H. Browne
*Assistant Examiner*—James M. Hewitt
(74) *Attorney, Agent, or Firm*—Roach, Brown, McCarthy & Gruber, P.C.; Kevin D. McCarthy

(57) ABSTRACT

A first conformable material having a three-dimensional shape and a first hypothermia and/or hyperthermia device, used as a pad for sleeping, lying down, or sitting, to maintain a desired temperature to the contacting surface of a body to the pad.

48 Claims, 5 Drawing Sheets

SUPPORTED HYPO/HYPERTHERMIA PAD

CLAIM OF PRIORITY

The present invention claims priority to U.S. Provisional patent application no. 60/128,433, filed on Mar. 30, 1999.

FIELD OF INVENTION

The present invention relates to a pad that provides hypo/hyperthermia properties to a person using the pad.

BACKGROUND OF THE INVENTION

In U.S. Pat. No. 5,336,708, Chen discloses a gelatinous elastomer composite article. These articles, as disclosed by Chen, "include: GMG, MGM, $MG_1G_2M$, $M_1M_2G_1G_2$, $M_2M_1G_1G_2$, $G_1MG_1G_2$, $MG_1G_2M$, $G_1G_2M$, $GM_1M_2G$, $G_1M_1G_2M_2M_1$, $M_1GM_2GM_3GM_4$, [sic] ect, where G = gel and M = material The subscript 1, 2, 3, and 4 are different and are represented by n which is a positive number. The material (M) suitable for forming composite articles with the gelatinous elastomer compositions can include foam, plastic fabric, metal, concrete, wood, wire screen, refractory material, glass, synthetic resin, synthetic fibers, and the like. Sandwiches of gel/material . . . are ideal for use as shock absorbers, acoustical isolators, vibration dampers, vibration isolators and wrappers. For example the vibration isolators can be [sic] use under research microscopes, office equipment, tables, and the like to remove background vibrations." U.S. Pat. No. 5,336,708, col. 3, lines 35–51. Chen further discloses, "generally the molten gelatinous elastomer composition will adhere sufficiently to certain plastics (e.g., acrylic, ethylene copolymers, nylon, polybutylene, polycarbonate, polystyrene, polyester, polyethylene, polypropylene, styrene copolymers, and the like) provided the temperature of the molten gelatinous elastomer composition is [sic] sufficient high to fuse or nearly fuse with the plastic. In order to obtain sufficient adhesion to glass, ceramics, or certain metals, sufficient temperature is also required (e.g., above 250° F. [121° C. ]" U.S. Pat. No. 5,336,708, col. 9, lines 8–18 (brackets added for consistency of temperature comparison).

Elkins in U.S. Pat. No. 4,884,304 describes a bedding system with selective heating and cooling of a person. That system has, from top to bottom, in order: a top mattress cover, a gas envelope and a multiplicity of liquid flow channels. The multiplicity of liquid flow channels is accomplished by a conventional hypo/hyperthermia blanket. The details of this conventional blanket are set forth in this patent. A problem with this system occurs when a person is on the mattress cover. When the person is on that mattress cover, the person has two sides: (1) a "contacting side" that touches the mattress cover and (2) the "exposed side" that does not touch the mattress cover. The person disperses the gas envelope and only certain portions of the contacting side contact the flow channels. As shown in FIG. 5 of that patent, the shoulders and other peripheral points of the contacting side of the person, such as arms, do not contact the flow channels. Thereby, that bedding system fails to transfer the desired temperature of the flow channels uniformly to all sections of the contacting side of the person.

M. Figman in U.S. Pat. No. 3,266,064, and von der Heyde in U.S. Pat. No. 5,887,304 illustrate conventional convective medium mattress system which essentially has a lower "box spring" and a mattress made of rubber, foam, or conventional mattress materials that an individual or object lies thereon. In each embodiment, the lower box spring has a cavity that the medium enters and distributes throughout. The medium then escapes from the cavity through apertures of the mattress.

A problem with these apertures 89 is that they kink 90 when an adult lies 22 thereon, as shown in FIG. 8. Please note that von der Heyde's system is designed for an infant, not an adult. And an infant is of such low weight that kinking is essentially nonexistent.

When kinking occurs, the medium is prevented from contacting the body. And when the medium does not contact the body, the medium is unable to treat the hypothermia or hyperthermia portions of the patient that contact the mattress, or even cool or heat the portions of the patient that contact the mattress.

The present invention solves this problem.

SUMMARY OF THE INVENTION

The present invention relates to a first conformable material having a three-dimensional shape and a first hypothermia and/or hyperthermia device.

BRIEF DESCRIPTION OF THE FIGURES

A preferred embodiment of the present invention is described in detail hereinafter with reference to the accompanying drawing, in which.

DETAILED DESCRIPTION OF THE INVENTION

Figure 1:
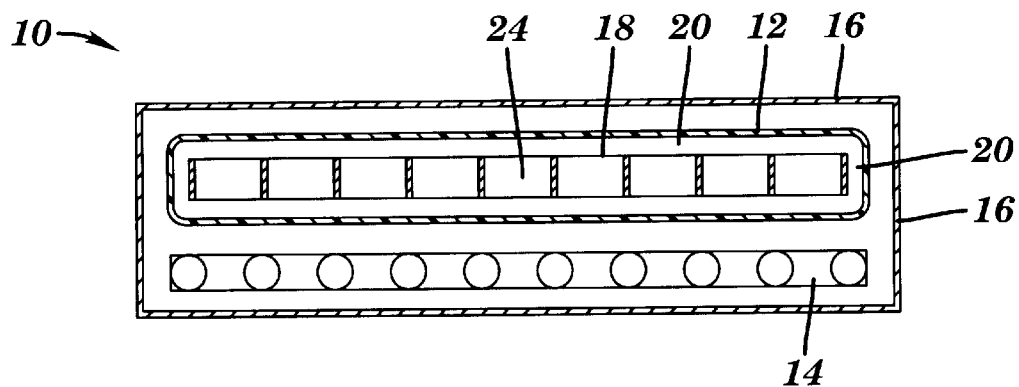
FIG. 1 is a cross-sectional view of the present invention.

FIG. 1 illustrates a pad 10 having a first sealable bag 12, a first hypothermia and/or hyperthermia device 14, and a pad cover 16. The bag 12 contains at least a first conformable material 18, and a thermally conductive medium 20. The thermal conductive medium 20 is any liquid or viscous gel that transfers energy generated by the device 14 to a patient (not shown). Examples of this liquid include water, water-based solutions, oil-based solutions, oils, alcohols, mixtures thereof, and viscous gels.

The conformable material 18 is any material having apertures that do not easily kink, preferably, a gelatinous elastomeric material. Examples of types of gelatinous materials, which are heat formable and heat reversible, are fully described in U.S. Pat. Nos. 4,369,284, 4,618,213, 5,262,468, 5,336,708, and 5,508,334, which are hereby incorporated by reference herein, and those made by Pittsburgh Plastic. The gelatinous materials manufactured by Pittsburgh Plastic are allegedly distinct from the patented types. This conformable material can be of any shape or design, so long as it has a three-dimensional shape that supports a patient or object on the pad 10.

The hypothermia and/or hyperthermia device 14 is any conventional hypo/hyperthermia blanket—an example of this blanket is the MUL-T-PAD® or the THERMACARE® blanket by Gaymar Industries, Inc. of Orchard Park, N.Y.— and its corresponding pump—the MEDI-THERM II® temperature regulator by Gaymar Industries, Inc. of Orchard Park, N.Y.—, an electric blanket, a cold compress, and a convective device. The convective device pumps or blows air or other gaseous medium (collectively "Air") having a predetermined temperature. The Air obtains the desired temperature in a conventional Air temperature regulator (for example, an air conditioner, a heat pump, a ThermaCare® blower unit, or the MEDI-THERM II® temperature regulator) and then circulates through a mesh screen like the Air Queen by Teijin, Inc. or a non-woven polymeric device having a plurality, of tubes with numerous apertures therein. The Air is then distributed throughout the entire pad 10. In any embodiment of device 14, the device 14 affects the temperature that a patient (not shown) or object (not shown) is exposed to, and, in some embodiments, the medium 20 that encompasses the conformable material 18.

The bag 12 is any sealable instrument that contains at least the thermally conductive medium 20 and conformable material 18 in place. Preferably, the bag 12 is plastic, and it can be sealed thermally, acoustically, by a zipper, zip locked, or even by Velcro®.

The pad cover 16 is any conventional material used to cover a pad 10. The pad cover 16 can encompass the entire pad 10, the preferred embodiment as shown, or cover the pad 10 like a conventional mattress sheet. In either embodiment the pad cover 16 can be cloth, leather, plastic or conventional cover material. The materials of the pad cover 16 allow the patient or object, on the pad 10, to feel the desired temperature of the pad 10 (Air or medium 20). The pad cover 16 can also allow moisture to pass through it. Thereby, it helps control the patient's temperature and prevents overcooling or overheating.

Figure 2:
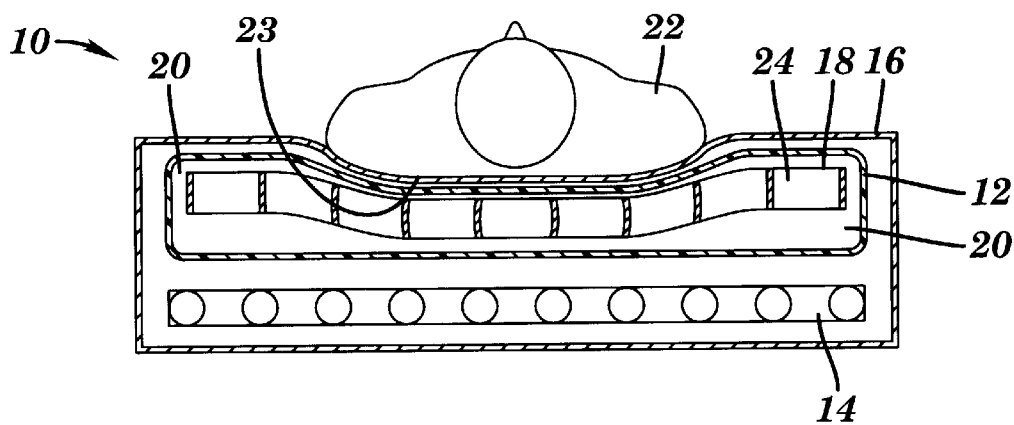
FIGS. 2–7 are alternative embodiments of FIG. 1.

Turning to FIG. 2, a patient 22 disperses a portion of the thermal conductive medium 20 in the bag 12 and contacts at least a portion of the conformable material 18 when the patient 22 lies on the pad 10. The conformable material 18 provides support to the patient 22, increases the effective surface contact of the pad 10 to the patient 22 to ensure greater desired thermal conductivity to the patient 22, maintains the stability of the bag 12, and reduces the pressure to the patient 22. By maintaining the stability of the bag 12, the conformable material 18 ensures the patient (or object) 22, on the pad 10, from directly contacting the hypothermia and/or hyperthermia device 14. In other words, the patient 22 does not "bottom out" to or directly contact the device 14.

Figure 9:
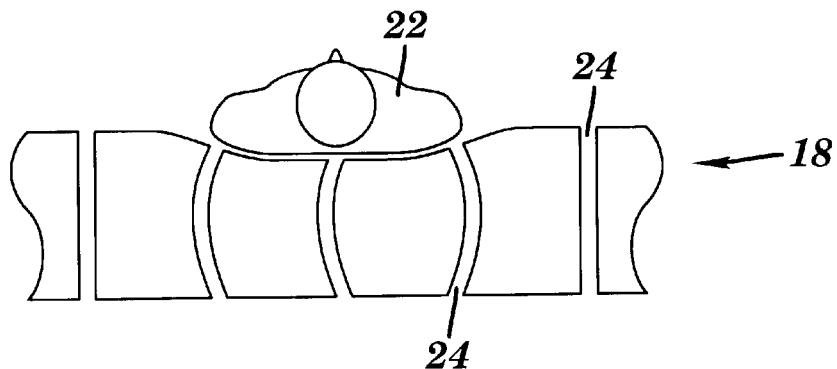
FIG. 9 is the present invention of an adult patient on a gelatinous elastomeric material with apertures.

In a preferred embodiment, the conformable material 18 has apertures 24. The apertures 24, in this embodiment, go from the bottom to the top of the material 18 and ensure the thermal conductive medium 20 is between the patient 22 and the hypothermia and/or hyperthermia device 14. However, in order to decrease, and essentially avoid, kinking— which is discussed above and, as a reminder, inhibits the medium 20 or the Air from contacting the patient— and which is common in many mattress materials, the preferred embodiment of the conformable material 18 is a gelantinous elastomer material. The gelantinous elastomer material has a structure design that admittedly bends and indents, as shown in FIG. 9, when a patient lies thereon, but does not kink. Thereby, the Air or medium can go through the apertures 24.

The hypothermia and/or hyperthermia device 14 heats or cools the thermal conductive material 20 and the patient 22 to a predetermined temperature. Since the thermal conductive material 20 contacts most, if not all, portions of the contacting side 23 of the patient 22, the material 20 ensures a uniform, or nearly uniform application of the predetermined temperature to the contacting side 23.

Figure 3:
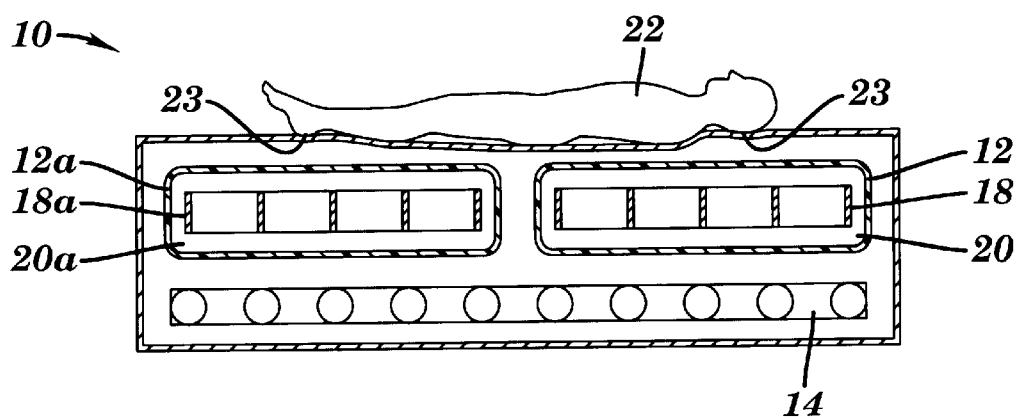

Turning to FIG. 3, the pad 10 contains at least a second bag 12a. The second bag 12a has at least a second conformable material 18a and a second thermal conductive material 20a. The second thermal conductive material 20a, the second bag 12a, and the second conformable material 18a can be the same or different materials as the previously listed corresponding elements 12, 18, 20.

Figure 4:
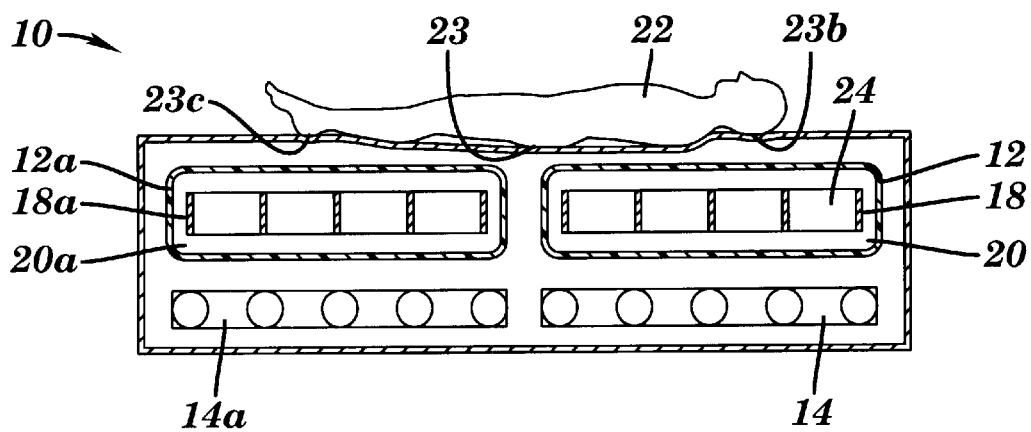

Turning to FIG. 4, an alternative embodiment of FIG. 3 is shown. A second hypothermia and/or hyperthermia device 14a is positioned under the second bag 12a. The second hypothermia and/or hyperthermia device 14a can be set at the same or different temperature as the hypothermia and/or hyperthermia device 14. Thereby, the first thermally conductive material 20 can apply one temperature to one portion of the contacting side 23b of the patient 22 and the second thermally conductive material 20a can apply the same or a different predetermined temperature to another portion contacting side 23c.

Figure 5:
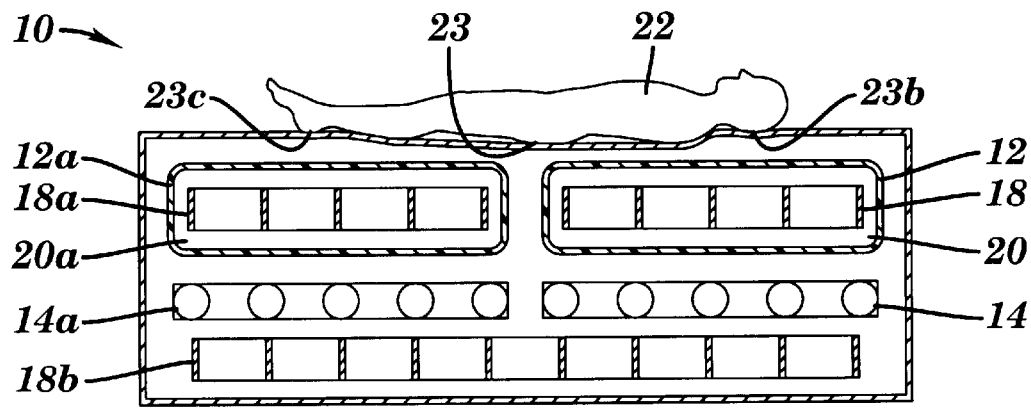

Turning to FIG. 5, an alternative embodiment of FIG. 4 is shown. A third conformable material 18b underlies the hypothermia and/or hyperthermia devices 14, 14a. This material 18b offers further support to the patient 22, maintains the stability of the bags 12, 12a, and further reduces the pressure to the patient 22. Obviously, this third material 18b can underlie, or alternatively be over. (not shown), the hypothermia and/or hyperthermia device(s) 14, 14a of FIGS. 1–4.

Figure 6:
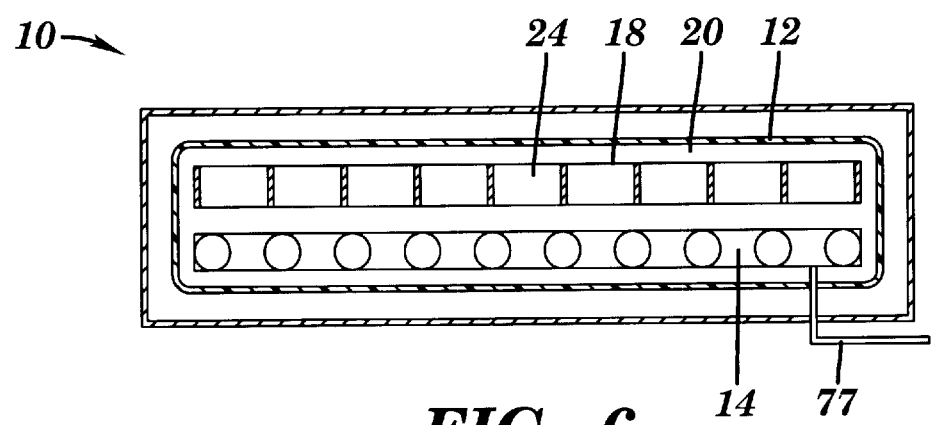

Turning to FIG. 6, an alternative embodiment of FIG. 1 is shown. The hyperthermia and/or hypothermia device 14 is within the bag 12 under, or alternatively be over (not shown), the conformable material 18 and surrounded by the thermal conductive medium 20. In this embodiment, the conventional inlet-outlet 77 of the device 14, i.e., the pump hoses of the MEDI-THERM II® system, protrudes from the sealed bag 12. Obviously this embodiment can be used in the other embodiments illustrated in FIGS. 3 and 4.

Figure 7:
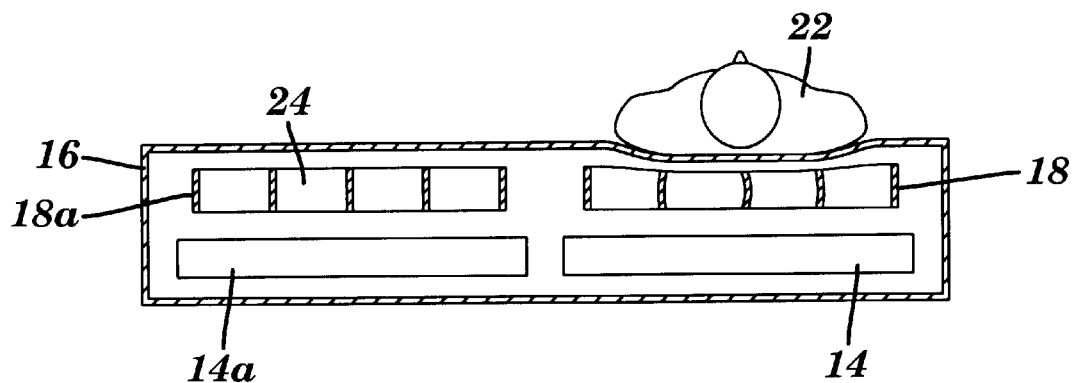
Figure 8:
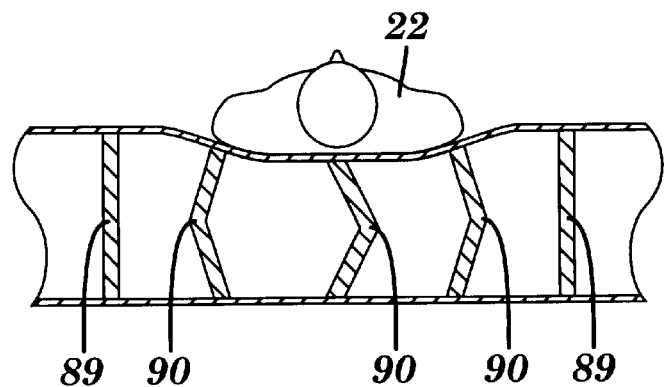
FIG. 8 is prior art of an adult patient on a conventional mattress system with apertures.

FIG. 7 illustrates an alternative embodiment of FIG. 1, wherein the conformable material is not inserted in a bag 12 or surrounded by a medium 20. In this embodiment, the hypothermia and/or hyperthermia device 14 is a convective unit and the Air goes through the apertures 24 of the gelatinous elastomer material 18.

Figure 12:
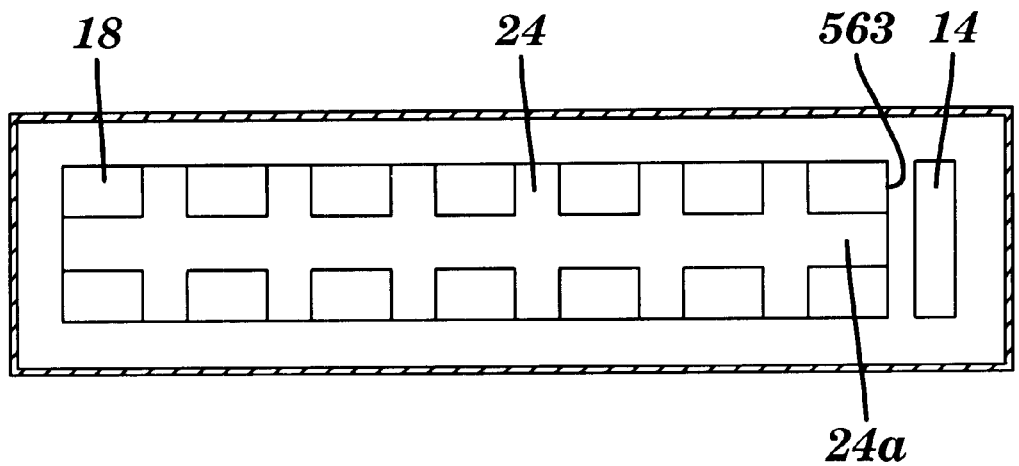
FIG. 12 is an alternative embodiment of FIG. 7.

FIG. 12 illustrates an alternative embodiment of FIG. 7. Along with the apertures 24, the conformable material 18 has a plurality of side apertures 24a interspaced between the upper wall and a lower wall of the material 18. Side apertures 24a receive Air and then distribute the Air throughout the conformable material 18.

In one embodiment (like that shown in FIG. 7) the device 14 is positioned below the conformable material 18. In yet another embodiment, as shown in FIG. 12, the device 14 is positioned at an end 563 of the conformable material 14. Thereby the Air goes into the side apertures 24a and is distributed throughout the conformable material 18 and apertures 24, to effect the patient's 22 temperature.

Figure 13:
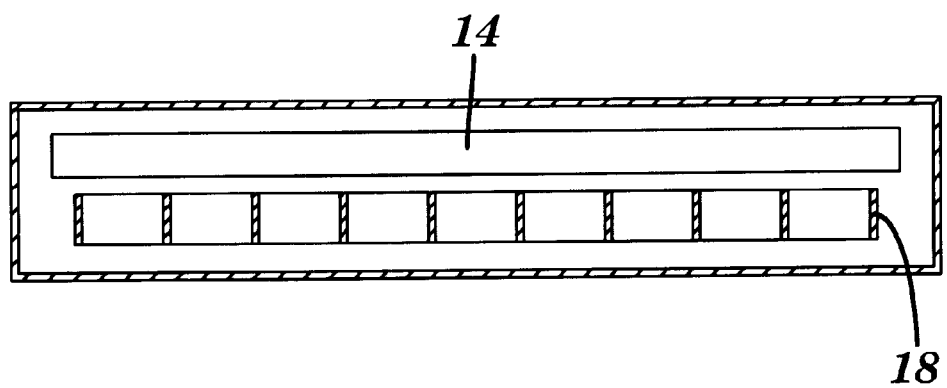
FIG. 13 is an alternative embodiment of FIG. 7.

Turning to FIG. 13, another embodiment of the present invention relates to the positioning of the hypothermia and/or hyperthermia device 14. The device 14 can also be positioned above the conformable material 18. The device 14 adjusts the temperature of the air within the pad 10, and that air cools or heats or maintains the temperature of the patient 22. The air also circulates through the pad 10 within the apertures 24 (and maybe 24a).

Figure 10:
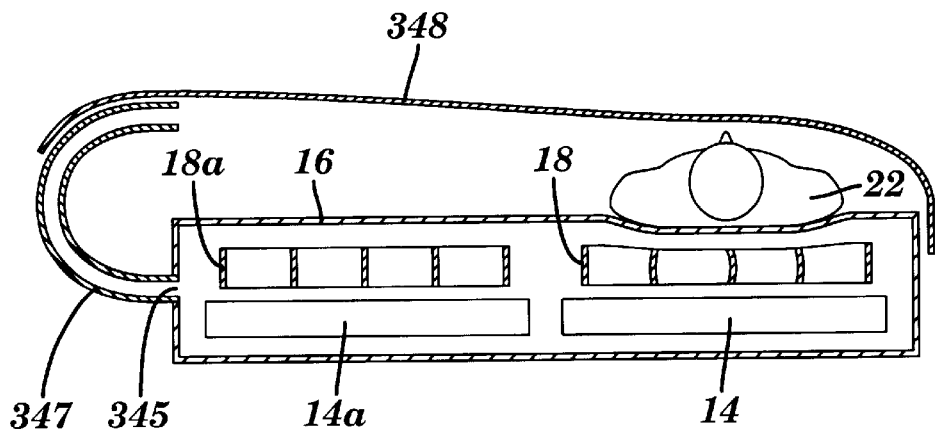
FIG. 10 is an alternative embodiment of the present invention with a conventional blanket.
Figure 11:
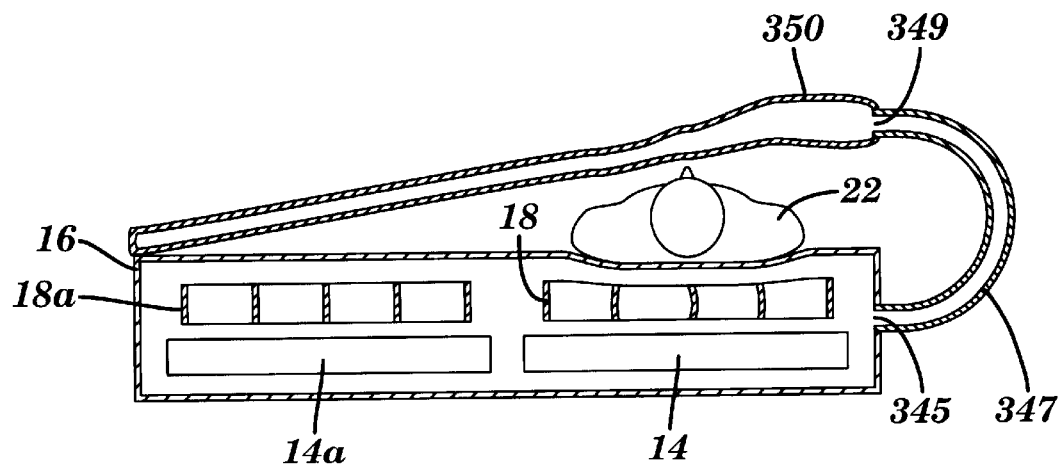
FIG. 11 is an alternative embodiment of FIG. 10 with a convective blanket.

Turning to FIGS. 10 and 11, the Air of FIG. 7 circulates under the cover 16, and escapes from, preferably predetermined, a gap 345 in the cover. Extending from gap 345 is a tube 347, flexible or not, that directs the Air under a conventional blanket 348, as shown in FIG. 10, or into an aperture 349 of a convective blanket 350, like the THERMACARE® blanket by Gaymar Industries, Inc., as shown in FIG. 11.

Alternatively, the pad cover 16 has a material that transfers the temperature to the patient but influences the Air to a predetermined gap(s) 345 in the pad 10. The predetermined gap(s) 345 can be located anywhere within the pad, i.e. at the bottom of the pad, a side of the pad as shown in FIGS. 10 and 11, if necessary, under the patient 22, or under the blanket 348 directly.

Turning to the method of the invention the preferred embodiment of the present invention is as an operating table pad and/or any other structure or object used in an operating.room or hospital-like mattress system, such as bed systems or seat cushions. An operating technician inserts at least one pad 10, having a hypothermia and/or hyperthermia device 14, and a conformable material 18, under a predetermined area of a patient 22. The technician then adjusts the device 14 to a predetermined temperature, in some instances the device 14 can only obtain one temperature. In either case, the device 14 adjusts the pad 10 to the predetermined temperature. At any time before or after the device 14 is initially adjusted to the predetermined temperature, the patient 22 lies on the pad 10 and the contacting side 23 of the patient 22 will be or is exposed to the predetermined temperature.

Although a particular preferred embodiment of the invention has been illustrated and described in detail for illustrative purposes, it will be recognized that variations or modifications of the disclosed apparatus, including the rearrangement of parts, lie within the scope of the invention defined by the claims.

The embodiments of the invention in which an exclusive property or privilege is claimed are defined as follows:

1. A pad comprising
    a first sealable bag, the first sealable bag has at least a first conformable material having a three-dimensional reformable shape and a first thermally conductive medium; and
    a first hypothermia and/or hyperthermia device near the first conformable material to alter the temperature of the first thermally conductive medium, wherein the first sealable bag and the first hypothermia and/or hyperthermia device are enclosed in a pad cover.

2. The pad of claim 1 wherein the first hypothermia and/or hyperthermia device is below the first conformable material.

3. The pad of claim 1 wherein the first hypothermia and/or hyperthermia device is above the first conformable material.

4. The pad of claim 1 wherein the first sealable bag and the first hypothermia and/or hyperthermia device are enclosed in a pad cover.

5. The pad of claim 1 wherein the first conformable material is a gelatinous elastomeric material.

6. The pad of claim 1 further comprising a a second sealable bag, the second sealable bag has at least a second conformable material and a second thermally conductive medium.

7. The pad of claim 1 wherein the first thermally conductive medium is a liquid.

8. The pad of claim 7 wherein the liquid is selected from the group consisting of water, a water-based solution, an alcohol, an oil solution, or mixtures thereof.

9. The pad of claim 6 wherein the second conformable material is a gelatinous elastomeric material.

10. The pad of claim 1 wherein the first thermally conductive medium is a viscous gel.

11. The pad of claim 1 wherein a third conformable material underlies the hypothermia and/or hyperthermia device.

12. The pad of claim 1 wherein the first hypothermia and/or hyperthermia device is a hypo/hyperthermia blanket.

13. The pad of claim 1 wherein the first hypothermia and/or hyperthermia device is an electric heating pad.

14. The pad of claim 1 wherein the first hypothermia and/or hyperthermia device is a cold compress.

15. The pad of claim 1 wherein the pad is used on an operating table.

16. The pad of claim 6 further comprising a second hypothermia and/or hyperthermia device positioned near the second conformable material, to provide the same or different temperature as the first hypothermia and/or hyperthermia device.

17. The pad of claim 16 wherein the second hypothermia and/or hyperthermia device is below the first conformable material.

18. The pad of claim 16 wherein the second hypothermia and/or hyperthermia device is above the first conformable material.

19. A method of using a pad comprising:
    inserting a first sealable bag into the pad, the sealable bag has at least a first conformable material and a first thermally conductive medium; and
    adjusting a first hypothermia and/or hyperthermia device positioned near the first conformable material to obtain a predetermined temperature for the thermally conductive medium, the first conformable material has a three-dimensional reformable shape.

20. The method of claim 19 wherein the hypothermia and/or hyperthermia device is below the first conformable material.

21. The method of claim 19 wherein the hypothermia and/or hyperthermia device is above the first conformable material.

22. The method of claim 19 wherein the first sealable bag and the first hypothermia and/or hyperthermia device are enclosed in a pad cover.

23. The method of claim 19 wherein the first conformable material is a gelatinous elastomeric material.

24. The method of claim 19 further comprising a second sealable bag, the second sealable bag has at least a second conformable material and a second thermally conductive medium.

25. The method of claim 19 wherein the first thermally conductive medium is a liquid.

26. The method of claim 25 wherein the liquid is selected from the group consisting of water, a water-based solution, an alcohol, an oil solution, or mixtures thereof.

27. The method of claim 24 wherein the first hypothermia and/or hyperthermia device is under the second conformable material.

28. The method of claim 19 wherein the first thermally conductive medium is a viscous gel.

29. The method of claim 19 wherein a third conformable material underlies the hypothermia and/or hyperthermia device.

30. The method of claim 19 wherein the first hypothermia and/or hyperthermia device is a hypo/hyperthermia blanket.

31. The method of claim 19 wherein the first hypothermia and/or hyperthermia device is an electric heating pad.

32. The method of claim 19 wherein the first hypothermia and/or hyperthermia device is a cold compress.

33. The method of claim 19 wherein the pad is used on an operating table.

34. The method of claim 24 further comprising the step of altering a second hypothermia and/or hyperthermia device, positioned near the second conformable material, to provide the same or different temperature as the first hypothermia and/or hyperthermia device.

35. The pad of claim 1 wherein the first hypothermia and/or hyperthermia device is within the first sealable bag.

36. The pad of claim 1 wherein the first hypothermia and/or hyperthermia device is below the first sealable bag.

37. The method of claim 19 wherein the first hypothermia and/or hyperthermia device is within the first sealable bag.

38. The method of claim 19 wherein the first hypothermia and/or hyperthermia device is below the first sealable bag.

39. The pad of claim 1 wherein the first hypothermia and/or hyperthermia device distributes convective energy.

40. The method of claim 19 wherein the first hypothermia and/or hyperthermia device distributes convective energy.

41. The pad of claim 6 wherein the first hypothermia and/or hyperthermia device is under the second conformable material.

42. The method of claim 24 wherein the second conformable material is a gelatinous elastomeric material.

43. The pad of claim 39 further comprising a blanket over the pad.

44. The pad of claim 43 wherein the convective energy is directed into the blanket.

45. The pad of claim 43 wherein the convective energy is directed below the blanket.

46. The method of claim 40 further comprising a blanket over the pad.

47. The method of claim 46 wherein the convective energy is directed into the blanket.

48. The method of claim 46 wherein the convective energy is directed below the blanket.

* * * * *